United States Patent
DuBois et al.

(10) Patent No.: US 11,154,338 B2
(45) Date of Patent: Oct. 26, 2021

(54) BONE FIXATION SYSTEMS AND METHODS

(71) Applicant: Alphatec Spine, Inc., Carlsbad, CA (US)

(72) Inventors: Nathaniel DuBois, Vista, CA (US); Scott Robinson, Encinitas, CA (US); Steven Leong, San Diego, CA (US); Jonathan T. Costabile, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 15/459,068

(22) Filed: Mar. 15, 2017

(65) Prior Publication Data

US 2017/0181781 A1    Jun. 29, 2017

Related U.S. Application Data

(60) Continuation-in-part of application No. 15/056,177, filed on Feb. 29, 2016, now Pat. No. 9,877,756, which is a division of application No. 13/010,392, filed on Jan. 20, 2011, now Pat. No. 9,271,770.

(51) Int. Cl.
| | |
|---|---|
| *A61B 17/80* | (2006.01) |
| *A61B 17/70* | (2006.01) |
| *A61F 2/44* | (2006.01) |
| *A61B 17/86* | (2006.01) |
| *A61F 2/30* | (2006.01) |

(52) U.S. Cl.
CPC ...... *A61B 17/8047* (2013.01); *A61B 17/7059* (2013.01); *A61B 17/8042* (2013.01); *A61F 2/447* (2013.01); *A61B 17/8605* (2013.01); *A61F 2002/30578* (2013.01)

(58) Field of Classification Search
CPC ............ A61B 17/8038; A61B 17/8047; A61B 17/8052
See application file for complete search history.

(56) References Cited

U.S. PATENT DOCUMENTS

| | | |
|---|---|---|
| 6,258,089 B1 | 7/2001 | Campbell et al. |
| 6,626,907 B2 | 9/2003 | Campbell et al. |
| 7,182,782 B2 | 2/2007 | Kirschman |
| D603,503 S | 11/2009 | Kriska et al. |
| D603,504 S | 11/2009 | Kriska et al. |
| D603,505 S | 11/2009 | Kriska et al. |
| D603,506 S | 11/2009 | Kriska et al. |
| D603,507 S | 11/2009 | Kriska et al. |
| D603,508 S | 11/2009 | Kriska et al. |
| D603,509 S | 11/2009 | Kriska et al. |
| D603,510 S | 11/2009 | Kriska et al. |

(Continued)

*Primary Examiner* — Jerrah Edwards
*Assistant Examiner* — Christine L Nelson
(74) *Attorney, Agent, or Firm* — Robert Winn

(57) ABSTRACT

A system and a bone fixation plate for preventing a fastener from rotating so as to prevent the fastener from backing out is provided. The system includes a plate having an opening. A retention member having an arm extending into the opening is configured to engage the head of the fastener so as to prevent the fastener from rotating after the fastener is seated within a vertebral body or implant. In one embodiment, the retention member engages a top surface of the head of the fastener. In another embodiment, the retention member engages a side wall of the head of the fastener.

16 Claims, 12 Drawing Sheets

(56) References Cited

U.S. PATENT DOCUMENTS

| | | |
|---|---|---|
| D603,511 S | 11/2009 | Kriska et al. |
| D603,961 S | 11/2009 | Kriska et al. |
| D603,962 S | 11/2009 | Kriska et al. |
| D603,963 S | 11/2009 | Kriska et al. |
| D603,964 S | 11/2009 | Kriska et al. |
| 7,641,701 B2 | 1/2010 | Kirschman |
| 7,655,028 B2 | 2/2010 | Kirschman |
| 7,955,362 B2 * | 6/2011 | Erickson ............ A61B 17/8052 606/280 |
| 8,062,367 B2 | 11/2011 | Kirschman |
| 8,372,152 B2 | 2/2013 | Kirschman |
| 8,734,493 B2 | 5/2014 | Kirschman |
| 8,795,370 B2 | 8/2014 | Kirschman |
| 8,821,553 B2 * | 9/2014 | Kirschman ........ A61B 17/7059 606/294 |
| 9,078,706 B2 | 7/2015 | Kirschman |
| 2005/0021032 A1 | 1/2005 | Koo |
| 2011/0118784 A1 * | 5/2011 | Baynham ........... A61B 17/7059 606/264 |
| 2013/0023992 A1 * | 1/2013 | Moskowitz ............. A61F 2/447 623/17.16 |

* cited by examiner

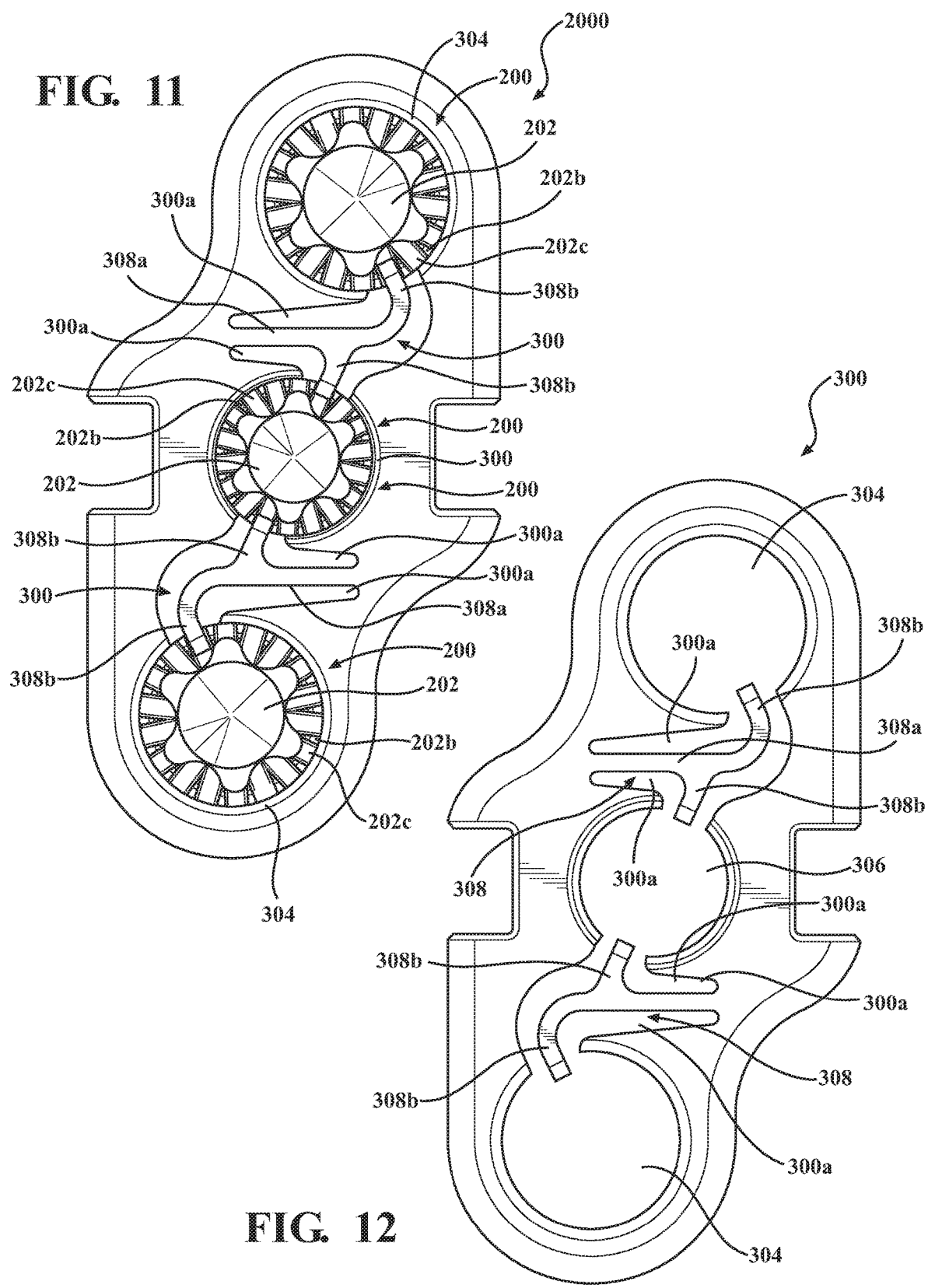

BONE FIXATION SYSTEMS AND METHODS

CROSS-REFERENCE TO RELATED APPLICATIONS

This application is a continuation in part of U.S. patent application Ser. No. 15/056,177 filed on Feb. 29, 2016, which is a divisional application of U.S. patent application Ser. No. 13/010,392 filed on Jan. 20, 2011 (now U.S. Pat. No. 9,271,770), both of which are incorporated herein in their entirety by reference.

FIELD OF THE INVENTION

The present disclosure generally relates to the field of spinal orthopedics, and more particularly to methods and systems for bone fixation plates for vertebrae.

BACKGROUND OF THE INVENTION

The spine is a flexible column formed of a plurality of bones called vertebrae. The vertebrae include a hollow cavity and essentially stack one upon the other, forming a strong column for support of the cranium and trunk of the body. The hollow core of the spine houses and protects the nerves of the spinal cord. The different vertebrae are connected to one another by means of articular processes and intervertebral, fibrocartilaginous bodies. The intervertebral bodies are also known as intervertebral disks and are made of a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and consequently irritated. The result may be chronic and/or debilitating back pain due to these spinal disorders.

One procedure for treating spinal disorders involves using substantially rigid plates to hold vertebrae in desired spatial relationships and orientations relative to each other. During the procedure, the spine can be approached anteriorly or posteriorly. In either case, holes are drilled and tapped in at least two of the vertebrae, to receive screws or other fasteners used to secure the plate. The holes are accurately positioned with reference to openings formed through the plate. In some cases the screws may be self-tapping. Typically the plate is curved about its longitudinal axis to facilitate contiguous surface engagement of the plate with the vertebrae. With the plate maintained against the vertebrae, the fasteners are secured within the holes. As a result, the plate maintains the attached vertebrae in a desired spacing and orientation with respect to each other.

One of the problems associated with bone fixation systems and methods is the tendency of screws or other fasteners to gradually work loose from the vertebrae after fixation of the bone plate. Slight shock or vibration of the vertebrae, due to walking, climbing stairs, or more vigorous activity by the patient following treatment increases this tendency, jeopardizing the integrity of fixation. Moreover, as the fasteners work loose, the outward protrusion of the heads over other components of the system can be a source of discomfort and present the risk of trauma to adjacent and surrounding soft tissue.

SUMMARY OF THE INVENTION

A bone fixation plate includes at least one opening formed in a plate that is configured to receive a fastener so as to secure the plate to a vertebral body and another opening configured to receive a fastener so as to secure the plate to an implant. A retention member extends into at least one of the openings and is configured to engage the fastener so as to prevent the fastener from rotating and becoming loose.

In one embodiment, the retention member is configured to engage a top surface of the head of the fastener. In another embodiment, the retention member is configured to engage a side wall of the head of the fastener.

In one embodiment, the plate includes a first opening spaced apart from a second opening, the first and second openings are configured to provide access for securing a fastener into a vertebral body. The plate further includes a third opening disposed between the first and second openings so as to provide access for securing a fastener to an implant.

A system for bone fixation includes a plate including a first opening, a second opening, and an opening between the first and the second openings; a retention member extending into the opening of the plate that is elastically deformable from a rest position to first and second toggled positions; a first screw including a head configured to elastically deform the retention member to the first toggled position; and a second screw including a head configured to elastically deform the retention member to the second toggled position.

In other features, the retention member further includes an arm extending from the plate into the opening and a first projection extending from the arm into the first opening. A second projection extends from the arm into the second opening.

In yet other features, the first projection blocks a portion of the first opening and the second projection blocks a portion of the second opening when the retention member is in the rest position. The first projection is inside the opening of the plate when the retention member is in the first toggled position. The second projection is inside the opening of the plate when the retention member is in the second toggled position. The first screw forces the first projection away from the first opening in the first toggled position. The second screw forces the second projection away from the second opening in the second toggled position.

A method for bone fixation includes the steps of inserting a first screw into a first opening of a plate to secure the plate to a vertebra, advancing the first screw to elastically deform a retention member formed in an opening of the plate, wherein the opening is in communication with the first opening, elastically deforming the retention member from a rest position to a first toggled position; and advancing the first screw until the retention member elastically returns to the rest position.

In other features, elastically deforming the retention member from the rest position to the first toggled position includes flexing an arm of the retention member. Advancing the first screw to elastically deform the retention member includes contacting a projection of the retention member with a head of the first screw.

In yet other features, the method further includes the steps of inserting a second screw into a second opening of the plate, advancing the second screw to elastically deform the retention member formed in the opening of the plate, wherein the opening is in communication with the second opening, elastically deforming the retention member from the rest position to a second toggled position; and advancing the second screw until the retention member elastically returns to the rest position. The first opening and the second opening are partially blocked when the retention member is in the rest position and one of the first and second openings is partially blocked when the retention member is in one of the first toggled position and the second toggled position.

BRIEF DESCRIPTION OF THE DRAWINGS

FIG. 11 is a top down view of the fixation plate shown in FIG. 10 showing the fastener engaged with the retention members.

FIG. 12 is top down view of the fixation plate shown in FIG. 10 in isolation.

DETAILED DESCRIPTION OF THE PREFERRED EMBODIMENTS

Some fasteners and bone fixation plates may include retention mechanisms that may prevent the screws from working loose from the plate and vertebra. However, many retention mechanisms are cumbersome and difficult to operate during surgical procedures. For example, some plates may have retention mechanisms that include additional hardware and features such as sliding tabs or projections, springs, and the like. The additional hardware adds weight and complexity to the plates and presents potential failure modes such as jammed tabs, broken springs, or other failures from the separate moving parts. The additional hardware may also require activation by the surgeon. That is, the surgeon may be required to find the activation point and twist or press a feature on the screw or plate to activate the retention mechanism. These additional steps require additional time and effort by the surgeon who is already under difficult working conditions such as low light and a confined surgical area.

Accordingly, a bone fixation system and method are provided to decrease weight and complexity while reducing the duration of the surgical procedure. The bone fixation plate of the present disclosure includes an integrated retention mechanism that is formed in the bone fixation plate itself. The retention mechanism includes geometry introduced into the bone fixation plate during the manufacturing process. For example, the geometry may be introduced by forming the retention mechanism out of a mold or cutting with a laser or plasma cutting technique. Thus, the retention mechanism requires no additional hardware on the bone fixation plate. The bone fixation plate of the present disclosure further includes a self-activating retention mechanism that automatically locks when a fastener is inserted to attach the plate to a vertebra.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Figure 1:
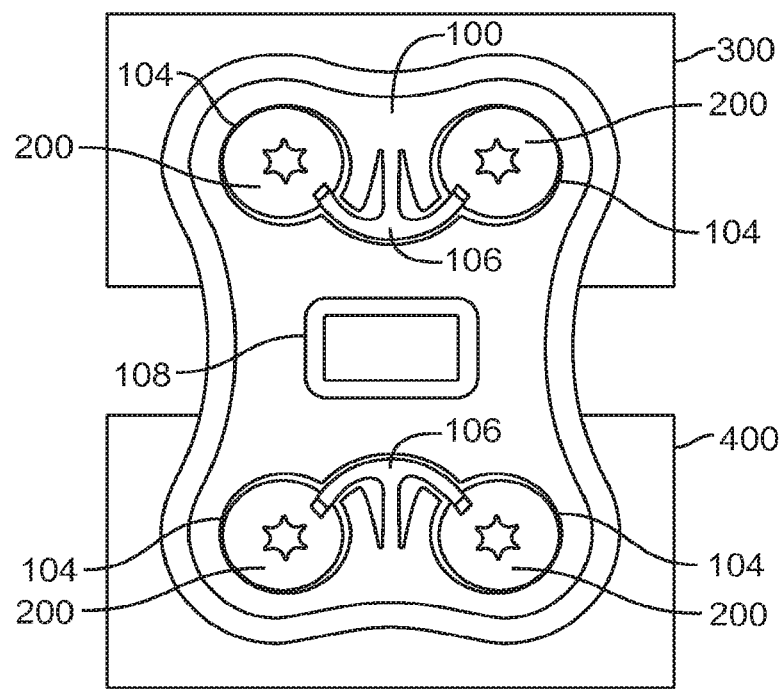
FIG. 1 is an elevational view of a bone fixation system attached to adjacent vertebrae according to the principles of the present disclosure.

Referring now to FIG. 1, a bone fixation plate 100, hereinafter referred to as the "plate," is configured to be attached to a first vertebra (not shown) and a second vertebra (not shown) using a fastener, illustratively shown as bone screws 200. The plate 100 may be substantially rectangular and include rounded sides and/or contoured surfaces to facilitate movement of tissue relative to the plate 100 after implantation in a patient. The plate 100 includes openings 104 formed in corners of the plate 100. The screws 200 pass through the openings 104 to attach to the first and second vertebrae. Retention mechanisms 106, formed between the openings 104 in the plate 100, keep the screws 200 from backing out of the respective first and second vertebrae after fixation. A window 108 may also be formed in the plate 100 to provide access to the space between the first vertebra and the second vertebra. Although the system and method shown herein may be used to fix together two vertebrae, it is understood that the system and method may be applicable to multiple vertebrae in excess of two. For example, the plate 100 may extend beyond the first and/or second vertebra to attach to other adjacent vertebrae and may include additional retention mechanisms disposed between additional pairs of openings and screws.

Figure 2:
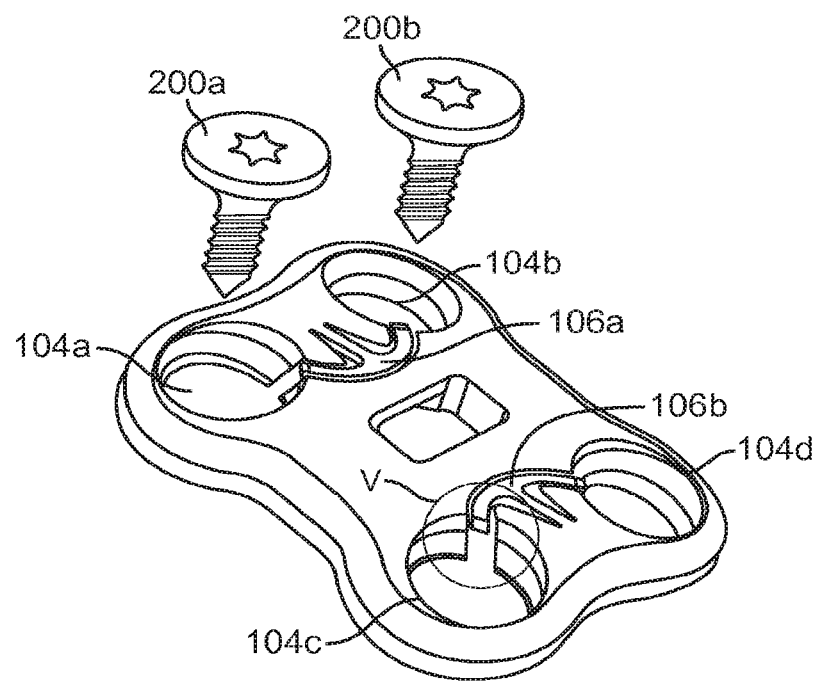
FIG. 2 is an exploded perspective view of the bone fixation system according to the principles of the present disclosure.

Referring now to FIG. 2, a first screw 200a may be inserted through a first opening 104a and a second screw 200b may be inserted through a second opening 104b. A first retention mechanism 106a is disposed between the first and second openings 104a and 104b and is configured to prevent both the first screw 200a and the second screw 200b from backing out of the plate 100 after fixation to the first vertebra. In one embodiment, the first retention mechanism 106a may be molded or machined from the material of the plate 100. Thus, the first retention mechanism 106a may be integral and continuous with the plate 100. In other embodiments, the first retention mechanism 106a may be attached to the plate 100 between the openings 104a and 104b. The first retention mechanism 106a may be attached by welding, snap fit, friction welding, or other forms of attachment.

For simplicity, one retention mechanism and one pair of adjacent openings are discussed in detail herein. However, it is understood by one in the art that the plate 100 of the present disclosure may include one or more retention mechanisms disposed between any pair of openings. For example, third and fourth openings 104c and 104d may be mirror images of the first and second openings 104a and 104b and configured to receive third and fourth screws, respectively. Similarly, a second retention mechanism 106b may be disposed between the third and fourth openings 104c and 104d. It may be readily understood by one in the art that the second retention mechanism 106b functions the same as the first retention mechanism 106a with respect to the third and fourth openings 104c and 104d. Thus, each of the retention mechanisms 106a and 106b may be referred to hereinafter as simply retention mechanism 106. Likewise, each pair of openings may be referred to hereinafter as simply first and second openings 104a and 104b.

Figure 3:
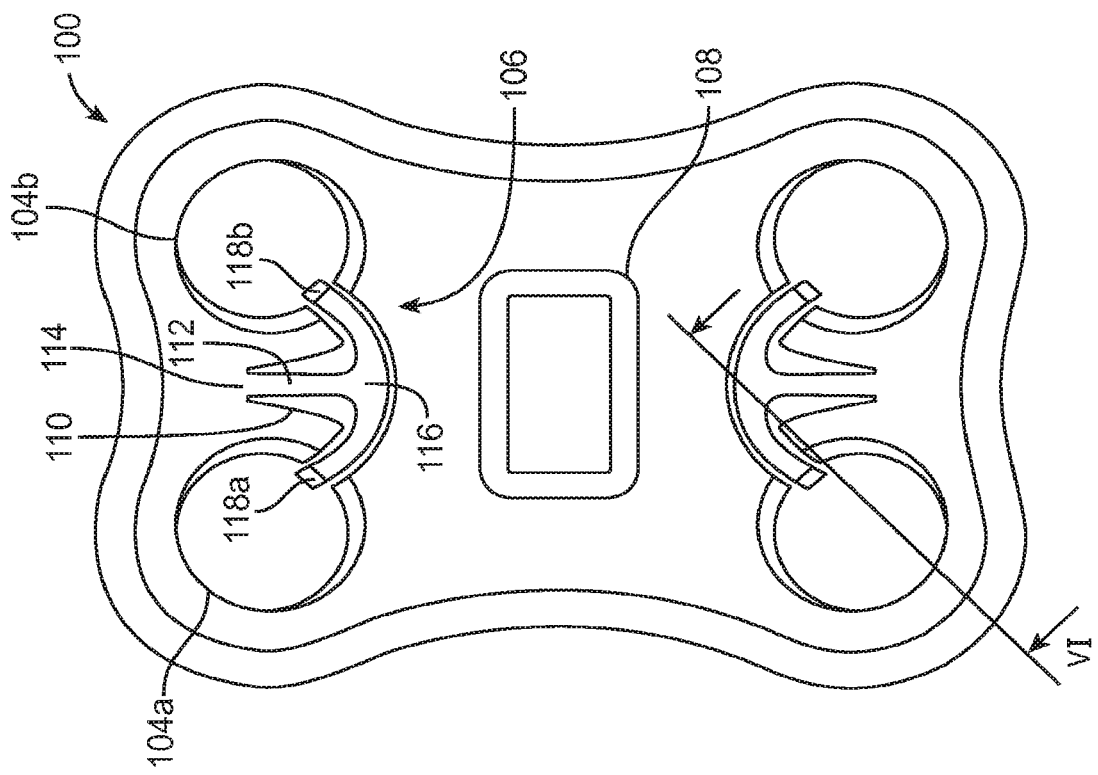
FIG. 3 is a top elevational view of the bone fixation plate according the principles of the present disclosure.

Referring now to FIG. 3, a top view of the plate 100 illustrates additional features of the retention mechanism 106 and openings 104a and 104b. The first opening 104a and the second opening 104b are formed in one end of the plate 100. The first and second openings 104a and 104b may be substantially circular and configured to receive the bone screws 200a and 200b respectively as shown in FIG. 2. The retention mechanism 106 is disposed in an opening 110 formed between the first and second openings 104a and 104b. The opening 110 may be irregular-shaped to conform to the geometry of the retention mechanism 106. In one embodiment, the opening 110 may be in communication with both the first opening 104a and the second opening 104b. That is, a continuous wall is shared between the first opening 104a, the second opening 104b, and the opening 110.

The retention mechanism 106 extends from the plate 100 into the opening 110 and is configured to lock the bone screws 200a and 200b to the plate 100. For example, the retention mechanism 106 may include a flexible arm 112 extending from the plate 100 into the opening 110. The flexible arm 112 may be attached to the plate at a proximal end 114 and include a distal end 116 cantilevered in the opening 110. A first projection 118a extends from the distal end 116 through the opening 110 and towards the first opening 104a. A second projection 118b extends from the distal end 116 through the opening 110 towards the second opening 104b. Thus, the retention mechanism 106 may resemble an inverted "T" shaped geometry or a nautical anchor. For example, the first and second projections 118a and 118b (collectively projections 118) may include curvature having a radius approximately equivalent to the length of the arm 112 from the proximal end 114 to the distal end 116.

Figure 4:
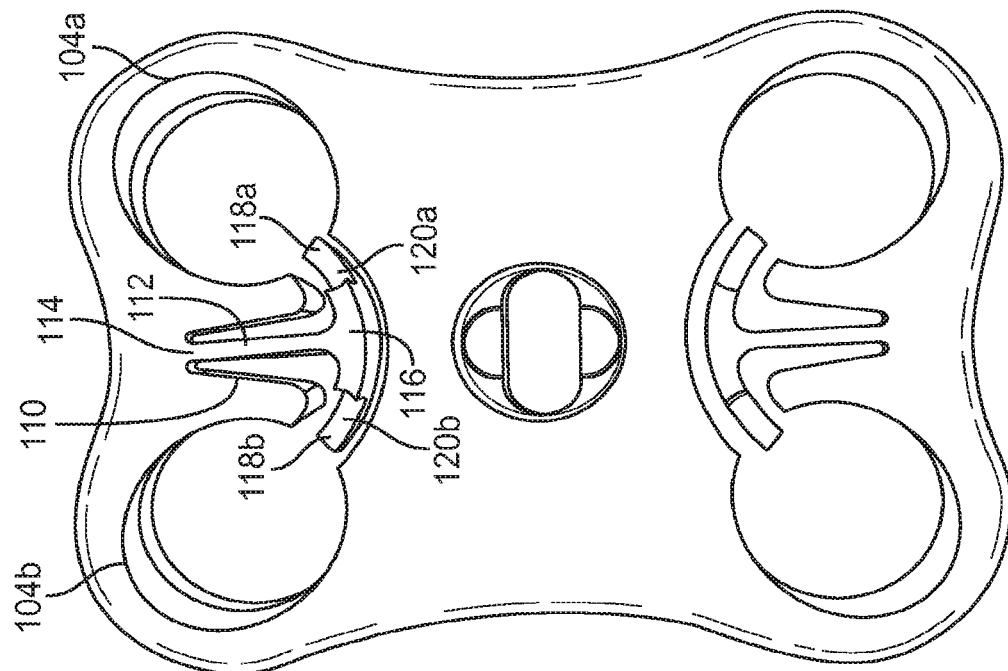
FIG. 4 is a bottom elevational view of the bone fixation plate according to the principles of the present disclosure.

Referring now to FIG. 4, a bottom view of the plate 100 illustrates additional features that enable retention of two bone screws with one retention mechanism 106. Each of the projections 118a and 118b includes a notch 120a and 120b respectively (collectively notches 120), formed at the ends of the projections 118. The notches 120 permit the projections 118 to slide over heads of the screws 200 after fixation to the vertebra as described below with reference to FIGS. 6A-6D and 7A-7E. The notches 120 may be configured to adjust the strength of the retention mechanism 106 by varying the thickness of the projections 118 and/or the arms 112. For example, the notches 120 may decrease the thickness of the retention mechanism 106 and thus increase flexibility. Alternatively, the retention mechanism 106 may be of a uniform thickness that permits the projections 118 to slide over heads of the screws 200.

The retention mechanism 106 is capable of elastically moving, bending, or toggling between at least three distinct positions. In a rest position, as shown in FIGS. 1-5, the arm 112 "rests" substantially equidistant from the first and second openings 104a and 104b. Both the first projection 118a and the second projection 118b extend partially into the first and second openings 104a and 104b respectively to retain first and second screws 200a and 200b within the openings 104a and 104b. From the rest position, the retention mechanism 106 may be toggled to a first toggled position and a second toggled position as discussed below.

Figure 5:
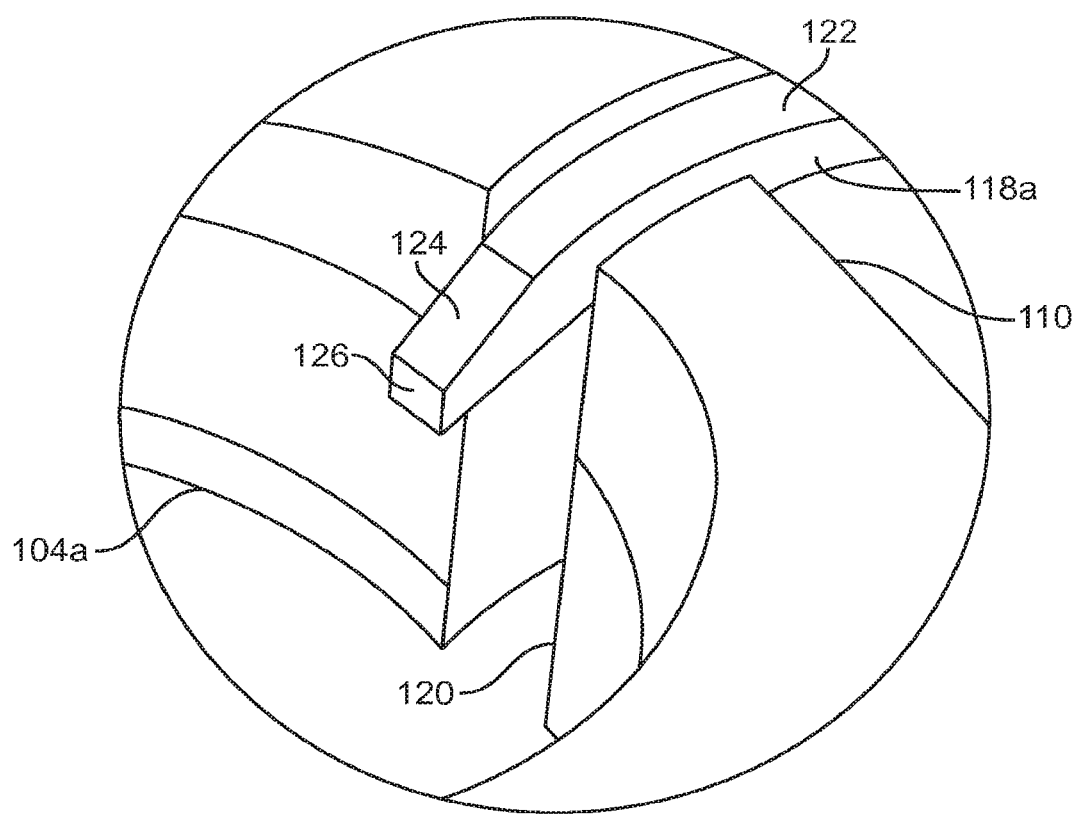
FIG. 5 is a partial perspective view of a retention mechanism in the bone fixation plate of FIG. 2 according to the principles of the present disclosure.

Referring now to FIG. 5, a portion of the retention mechanism 106b of FIG. 2, and more particularly the first projection 118a is shown in greater detail. The first projection 118a extends through a mouth 120 in the opening 110 and into the first opening 104a. The mouth 120 provides communication between the opening 110 and the opening 104a. The first projection 118a may include a top surface 122 that substantially conforms to a top surface 123 of the plate 100. The first projection 118a may include a taper 124 that decreases in thickness from the top surface 122 to a tip 126 on the distal end of the first projection 118a. The taper 124 may facilitate engagement with the screw 200 as illustrated in FIGS. 6A-6D.

Figure 6A:
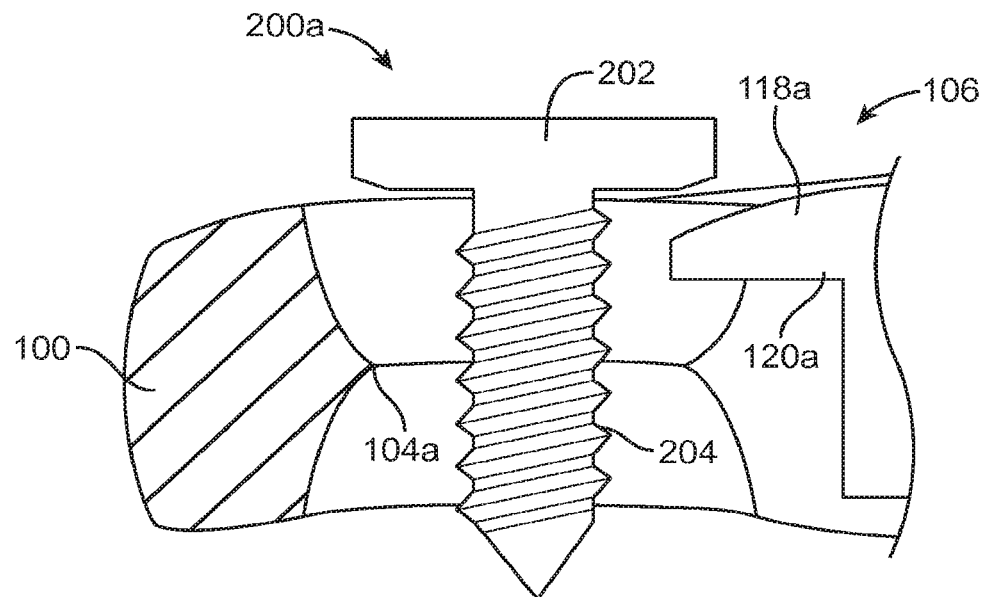
FIGS. 6A-6D are partial cross-sectional views of a portion of the bone fixation plate along line VI of FIG. 3 and a bone screw according to the principles of the present disclosure.
Figure 6B:
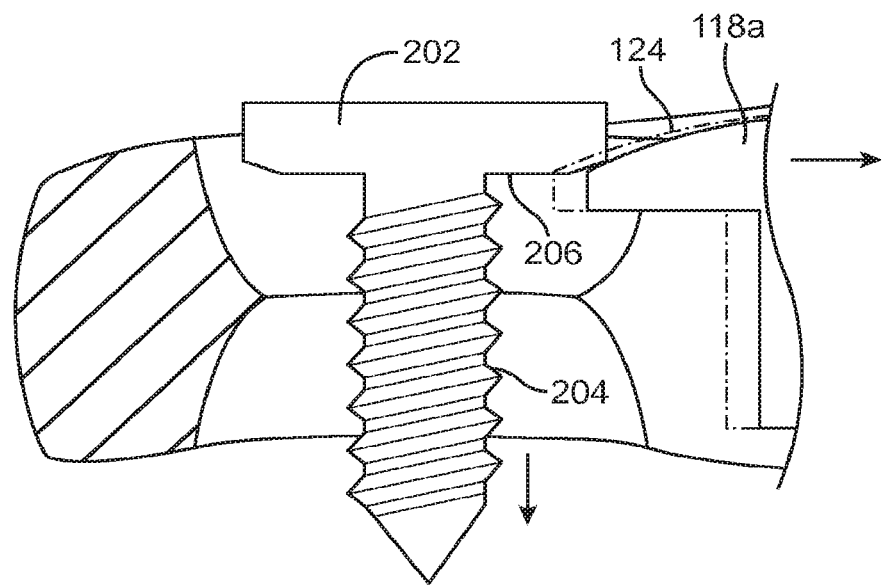

Referring now to FIGS. 6A-6D, engagement between the screw 200 and the retention mechanism 106 are shown in greater detail. The screw 200 includes a head 202 and a threaded shaft 204. The head 202 may be driven by a screwdriver such that the shaft 204 penetrates the vertebra (not shown) to secure the plate 100. In FIG. 6A, the screw 200 is inserted into the first opening 104a. As the screw 200 advances through the first opening 104a, a bottom surface 206 of the head 202 moves towards the retention mechanism 106. As the head 202 is driven, the shaft 204 engages more of the vertebra, and the bottom surface 206 begins to contact the taper 124 of the first projection 118a as shown in FIG. 6B. The bottom surface 206 exerts a downward force on the retention mechanism 106. The downward force pushes against the taper 124 which transfers a portion of the downward force to the retention mechanism 106. The flexible arm 112 (not shown) bends due to the force, and the projection 118a begins to move away from the first opening 104a, as illustrated in detail in FIG. 6B.

Figure 6C:
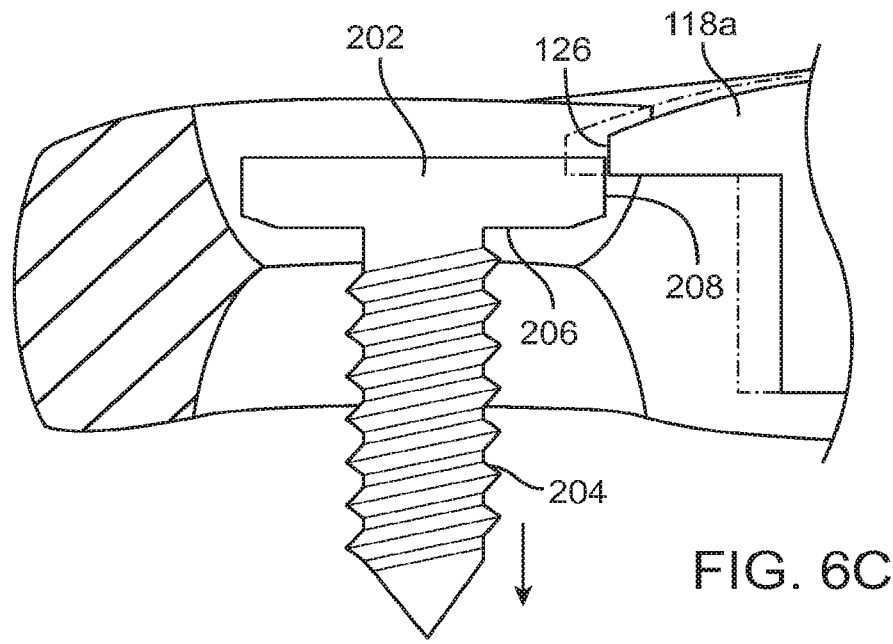
Figure 6D:
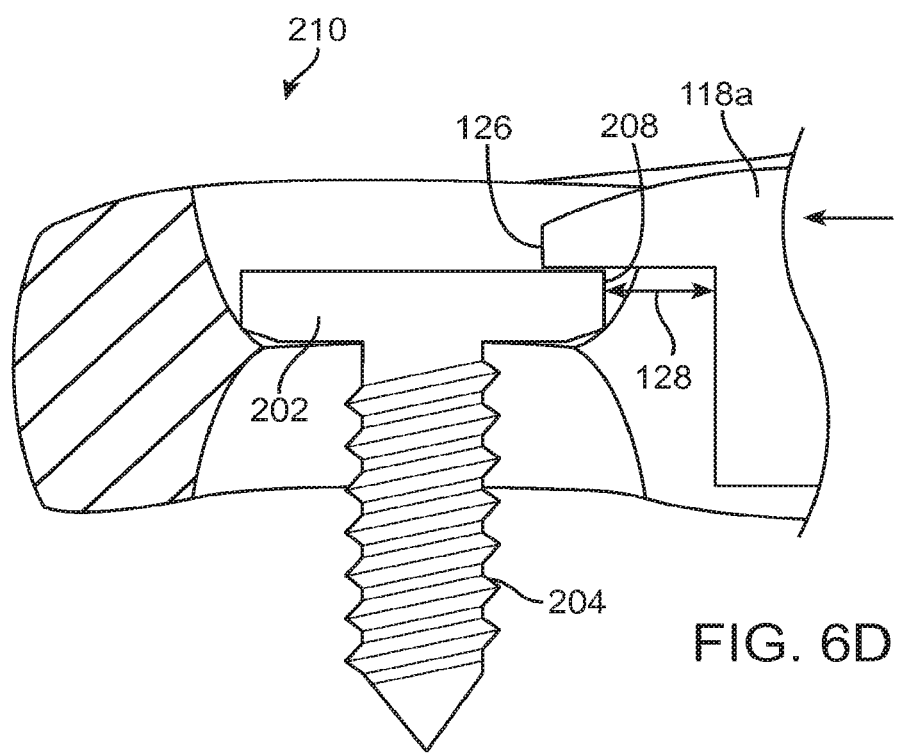

Continuing now with FIG. 6C, as the screw 200 continues to be driven into the vertebra, the bottom surface 206 passes by the taper 124 and a side wall 208 of the head 202 contacts the tip 126 of the projection 118a. At this point, the retention mechanism 106 is in the first toggled position. In a toggled position, the arm 112 of the retention mechanism 106 may be fully bent towards the opposing opening as will be discussed in detail below. The screw 200 continues to be driven into the vertebra until fully seated in FIG. 6D. Once the screw 200 is fully seated, the retention mechanism 106 returns to the rest position. Now, the tip 126 of the projection 118a extends over a top surface 210 of the head 202 of the screw 200 and the bottom surface 206 may contact a lip 127 in the opening 104a. Thus, the retention mechanism 106 prevents the screw 200 from backing out from the plate 100. Although the top surface 210 of the screw 200 contacts the projection 118a in FIG. 6D, a gap may remain after the screw 200 attaches to a vertebra. As can be seen in FIG. 6D, a gap 128 may remain between the projection 118a and the side wall 208 of the screw 200 once the retention mechanism 106 has returned to the rest position. The gap 128 permits the retention mechanism 106 to bend towards the first opening 104a when the second screw 200b is inserted into the second opening 104b as discussed below with reference to FIGS. 7A-7E.

Figure 7A:
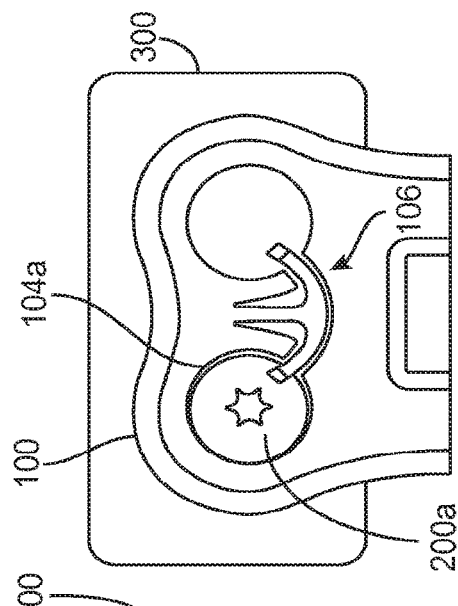
FIGS. 7A-7E are partial top elevational views of one end of the bone fixation system as the end is attached to one of the vertebrae.
Figure 7B:
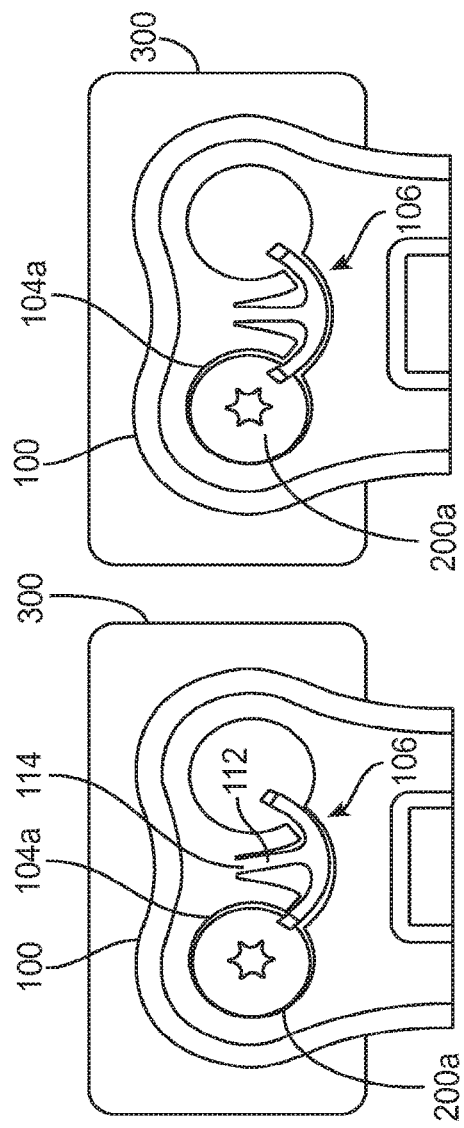
Figure 7C:
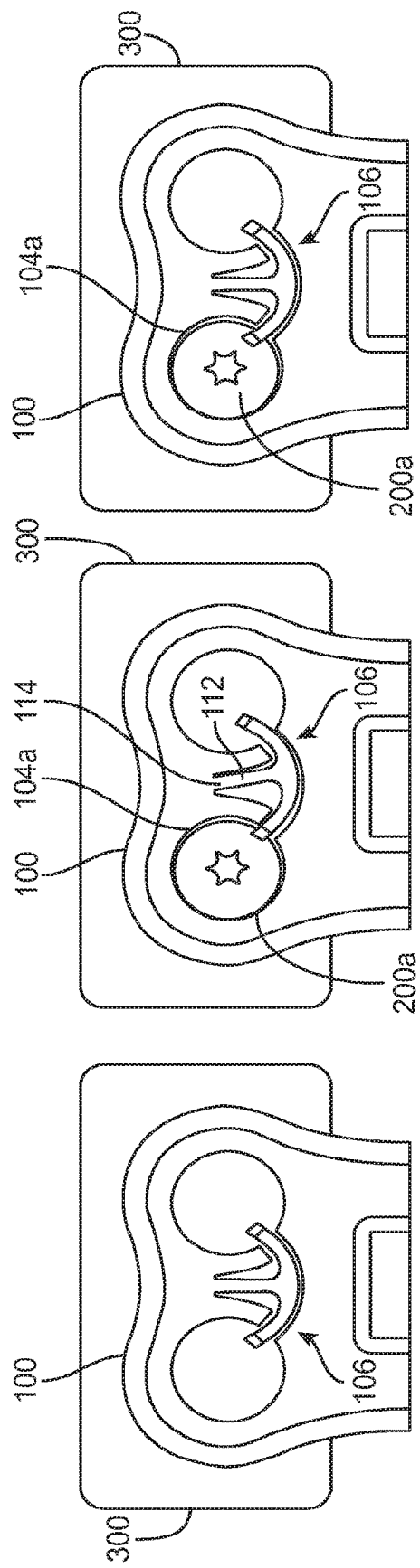

Referring now to FIGS. 7A-7E, the bone fixation system and method are shown in greater detail by a series of partial top views. In FIG. 7A, a first half of the plate 100 is shown positioned over the first vertebra. The retention mechanism 106 is in the rest position with no screws in place. In FIG. 7B, the first screw 200a is inserted into the first opening 104a and driven into the vertebra. As described with respect to FIGS. 6B-C, the bottom surface 206 of the screw 200a contacts the taper 124 causing the retention mechanism 106 to bend about the proximal end 114 of the arm 112. The arm 112 elastically bends to the first toggled position before the first screw 200a is fully seated in the first opening 104a. In FIG. 7C, the first screw 200a is fully seated in the first opening 104a. The retention mechanism 106 returns to the rest position to prevent the first screw 200a from backing away from the plate 100. The tip 126 of the projection 118a extends over the top surface 210 of the screw head 202, as shown in FIG. 6D. Thus, the screw head 202 is locked between the projection 118a and the lip 127.

Figure 7D:
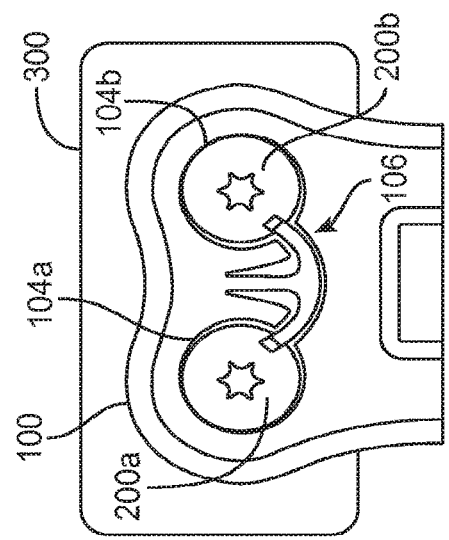
Figure 7E:
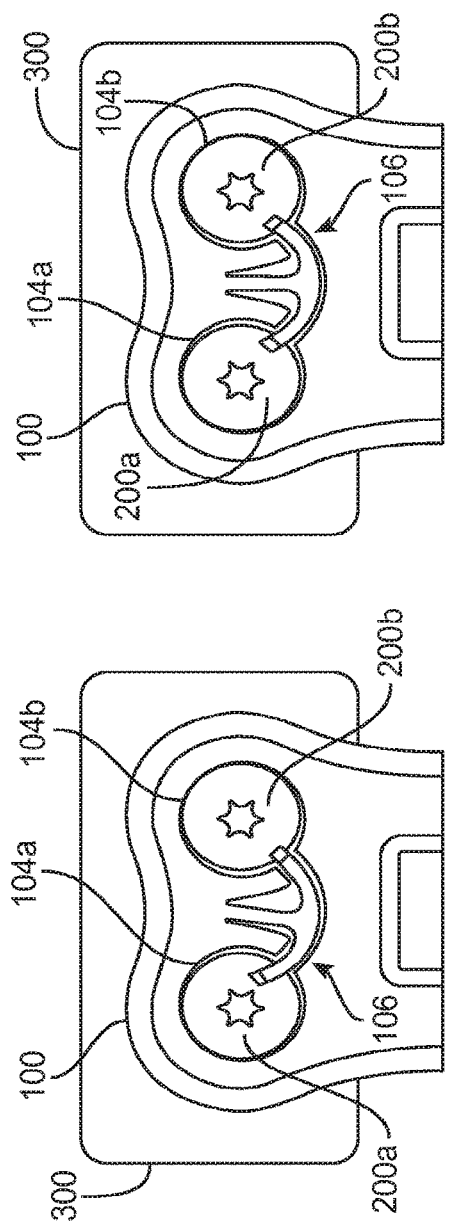

Referring now to FIG. 7D, the second screw 200b is inserted into the second opening 104b and driven into the vertebra. As described with respect to FIGS. 6B-C, the bottom surface 206 of the screw 200b contacts the taper 124 on the distal end of the projection 118b causing the retention mechanism 106 to bend about the proximal end 114 of the arm 112. The arm 112 elastically bends to the second toggled position before the second screw 200b is fully seated in the second opening 104b. In FIG. 7E, the second screw 200a is fully seated in the second opening 104b. The retention mechanism 106 returns to the rest position to prevent the second screw 200b from backing away from the plate 100. The tip 126 of the projection 118b extends over the top surface 210 of the screw head 202 of the second screw 202b. Thus, the screw head 202 is locked between the projection 118b and a corresponding lip 127 of the second opening 104b.

Figure 8:
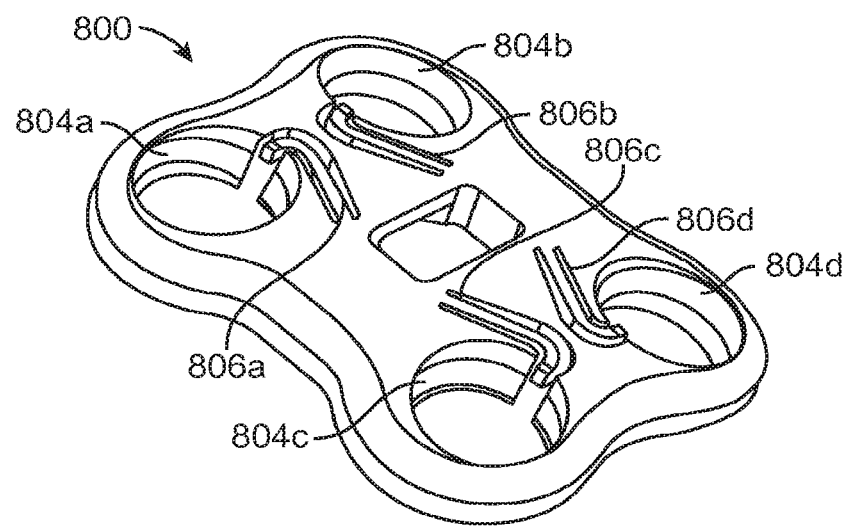
FIG. 8 is a perspective view of another bone fixation plate according to the principles of the present disclosure.
Figure 9:
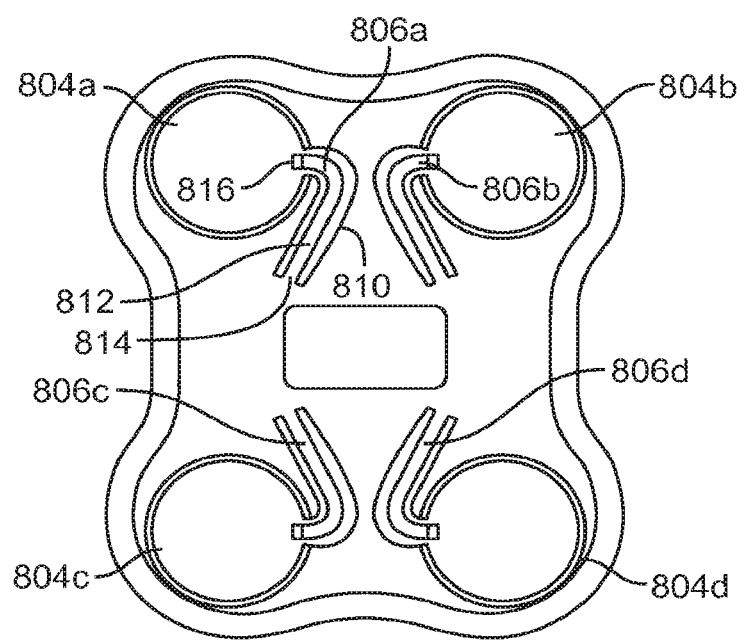
FIG. 9 is a top view of another bone fixation plate according to the principles of the present disclosure.

FIGS. 8 and 9 illustrate another embodiment of a bone fixation plate 800 that includes separate retention mechanisms 806a-d (collectively retention mechanisms 806) for each opening 804a-d (collectively openings 804). For example, a first retention mechanism 806a is disposed between first and second openings 804a and 804b and is configured to prevent a first screw (not shown) in the first opening 804a from backing out of the plate 800 after fixation to a vertebra. The first retention mechanism 806a may be molded or machined from the material of the plate 800. Thus, the first retention mechanism 806a may be integral and continuous with the plate 800. In other embodiments, the first retention mechanism 806a may be attached to the plate 100 between the openings 804a and 804b. The first retention mechanism 806a may be attached by welding, snap fit, friction welding, or other forms of attachment. A second retention mechanism 806b is disposed between the second opening 804b and the first retention mechanism 806a and is configured to prevent a second screw (not shown) in the second opening 804b from backing out of the plate 800 after fixation to the vertebra.

For simplicity, two retention mechanisms and one pair of adjacent openings are discussed in detail herein. However, it is understood by one in the art that the plate 800 of the present disclosure may include two retention mechanisms disposed between any pair of openings. For example, third and fourth openings 804c and 804d may be mirror images of the first and second openings 804a and 804b and configured to receive third and fourth screws, respectively. Similarly, a third retention mechanism 806c, may be disposed between the third and fourth openings 804c and 804d and a fourth retention mechanism 806d may be disposed between the fourth opening 804d and the third retention mechanism 806c.

Referring now to FIG. 9, a top view of the plate 800 illustrates additional features of the retention mechanism 806 and openings 804a and 804b. The first opening 804a and the second opening 804b are formed in one end of the plate 100. The first and second openings 804a and 804b may be substantially circular and configured to receive the bone screws 200a and 200b respectively (not shown), similar to openings 104a and 104b as shown in FIG. 2. Each retention mechanism 806 is disposed in a separate opening 810 formed around each retention mechanism 806. The openings 810 may be irregular-shaped to conform to the geometry of the retention mechanism 806. In one embodiment, each opening 810 may be in communication with a neighboring opening 804. That is, a continuous wall is shared between one opening, such as opening 804a and one opening 810.

Each retention mechanism 806 extends from the plate 800 into the opening 810 and is configured to lock one bone screw to the plate 800. The retention mechanism 806 includes a flexible arm 812 extending from the plate 800 into the opening 810. The flexible arm 812 may be attached to the plate at a proximal end 814 and include a distal end 816 cantilevered in the opening 810. A projection 818 extends from the distal end 816 through the opening 808 and towards the opening 804. Thus in the present embodiment, the retention mechanism 806 may resemble a "J" shaped geometry or a cane. For example, the projection 818 may include curvature having a radius equivalent to the length of the arm 812 from the proximal end 814 to the distal end 816.

The retention mechanisms 806 function similar to the retention mechanism 106 as depicted in FIGS. 6A-6D. That is, each retention mechanism 806 includes a taper on the projection 818 that comes in contact with a bottom surface of a screw when the screw is driven into a vertebra. As the screw is driven further into the vertebra, the retention mechanism 806 contacts an outer wall of the head of the screw and moves from a rest position to a toggled position. However, in the present embodiment, each retention mechanism 806 locks one screw rather than two screws as retention mechanism 106. Thus, the retention mechanism 806 in the present example may be toggled between the rest position as depicted in FIGS. 8 and 9 and one toggled position similar to the first toggled position of the retention mechanism 106.

Figure 10:
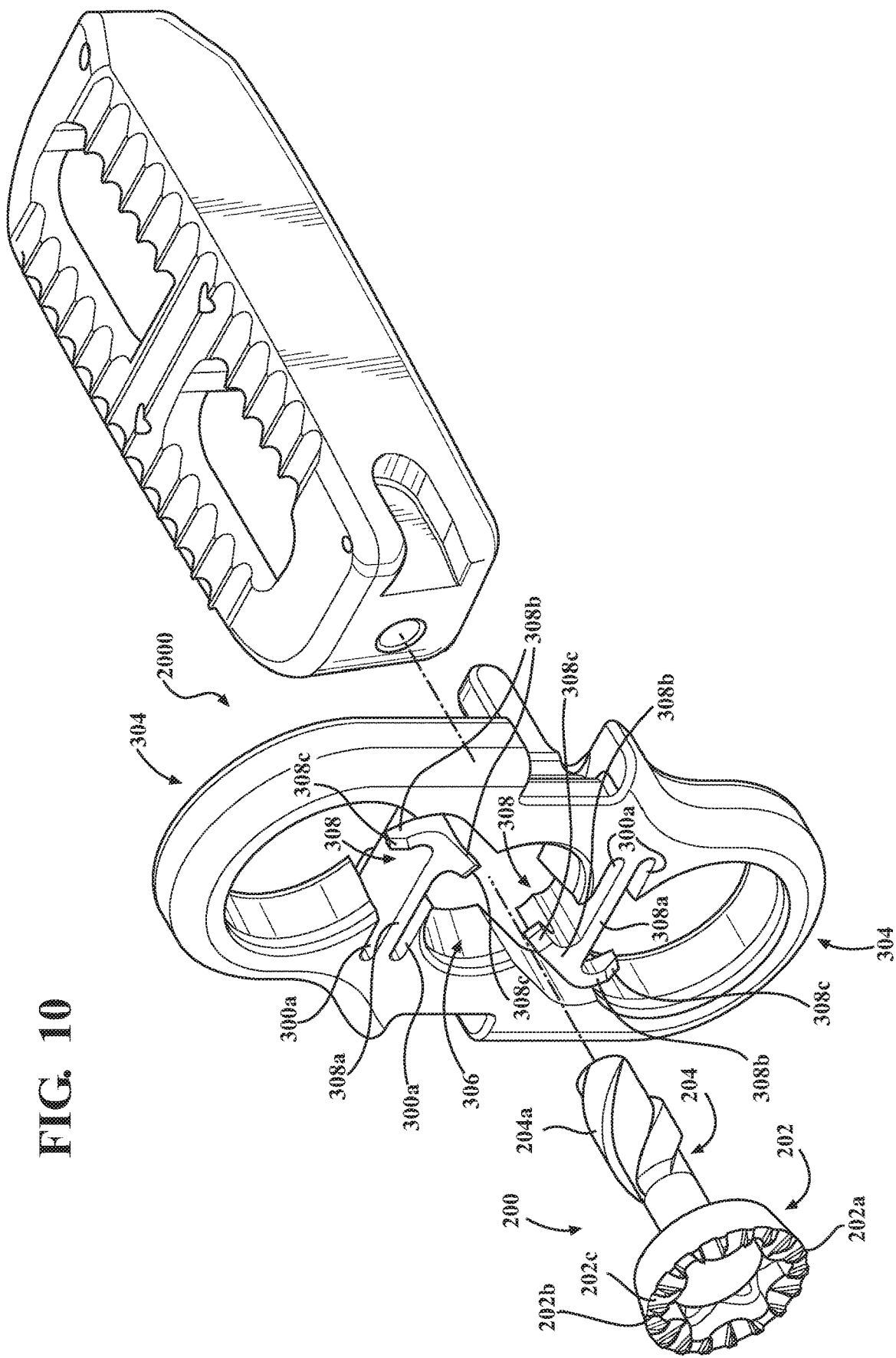
FIG. 10 is a perspective view of another embodiment of a fixation plate having a retention member configured to engage a top surface of a fastener.

With reference now to FIGS. 10-16 an aspect of the fixation plate is provided wherein the retention member is configured to engage the fastener so as to prevent the fastener from rotating. With reference first to FIG. 10 the fixation plate 300 is configured to be attached to a first vertebra (not shown) and a second vertebra (not shown) using a fastener, for example, and without limitation, bone screws 200 depicted in FIGS. 1-2. The fixation plate 300 may be substantially rectangular and include rounded sides and/or contoured surfaces to facilitate movement of tissue relative to the plate 300 after implantation in a patient.

The plate 300 is illustratively shown having a pair of vertebral openings 304 formed opposite ends of the plate 300. The vertebral openings 304 are configured to allow the screws 200 to find purchase in a vertebral body. A central opening 306 is disposed between the vertebral openings 304. The central opening 306 is configured to allow a screw 200 to find purchase in an implant 1000.

The plate 300 includes at least one retention member 308. For illustrative purposes, the plate 300 includes a pair of retention members 308. The retention members 308 are formed between the vertebral openings 304 and the central opening 306. The retention members 308 are configured to engage the screws 200 so as to prevent the screws 200 from rotating and backing out of the respective vertebral openings 304 and the central opening 306.

FIG. 10, shows a screw 200 being introduced into the central opening 306, it should be appreciated that the screw 200 shown in FIG. 10 may be modified for use to find purchase in vertebral bodies. In particular, the screws illustratively shown in FIG. 11 all have the same head 202 but the shafts 204 of the screws may differ to accommodate the intended use. For instance, the thread pitch and shape of the screw shown in FIG. 10 is intended to couple with an implant. However, the thread pitch and shape of screws intended to find purchase in a vertebral body may differ.

In one embodiment, the retention members 308 may be molded or machined from the material of the plate 300. Thus, the retention members 308 may be integral and continuous with the plate 300. In other embodiments, the retention members 308 may be formed separately from the plate 300 and attached to the plate 300 between the vertebral openings 304 and the central opening 306. For instance, the retentions members 308 may be attached by welding, snap fit, friction welding, or other forms of attachment.

For simplicity, the operation and structure of one retention member 308 and the central opening 306 and one vertebral opening 304 is discussed in detail herein. However, it should be appreciated by those skilled in the art that the discussion of one retention member 308 is sufficient to describe and enable the construction of the other retention members. It should be further appreciated that the embodiments described herein show two vertebral openings 304 and one central opening 306, but the plate 300 may be modified to include additional openings without deviating from the scope of the appended claims. For instance, the plate 300 may have four openings as shown in FIGS. 1-4.

Referring again to FIG. 10 and also to FIG. 12, a perspective view and a top down view, respectively, of the plate 100 illustrates additional features of the retention member 300. The retention member 308 is a resilient material having a stem 308a and an arm 308b. The arm 308b is generally orthogonal to the stem 308a. The opposing sides of the stem 308a is spaced apart from the body of the plate 300 so as to form two slots 300a on each side of the stem 308a. The slots 308a allow the stem 308a to flex. The arm 308b extends into a respective opening. For illustrative purposes, the retention member 308 is shown as having two arms 308b extending outwardly and opposite each other into a respective vertebral opening 304 and central opening 306 so as to form the general shape of a "T".

The screw 200 includes a head 202 having a top surface 202a configured to engage an arm 308b of the retention member 308. In one embodiment top surface 202a includes a plurality of nubs 202b spaced apart from each other so as to form detents 202c. The arms 308b may include a taper 308c. The taper 308c may facilitate the introduction of the screw 200 into the vertebral body or the implant, as the case may be, by facilitating the biasing of the retention member 308 about the stem 308a. The screws include a shaft 204 with a thread 204a. As described above, the thread 204a is shown configured to couple with an implant, but may be modified to find purchase with a vertebral body.

FIG. 11 shows each of the openings 304, 306 with screws 200 disposed therein. In particular, each arm 308b is seated in a respective detent 202c and held therein by surrounding nubs 202. Accordingly, the arms 308b are engaged with a top surface 202a of a respective screw 200 so as to prevent the screw from rotating and thus backing out of the implant or vertebral body as the case may be.

Figure 13A:
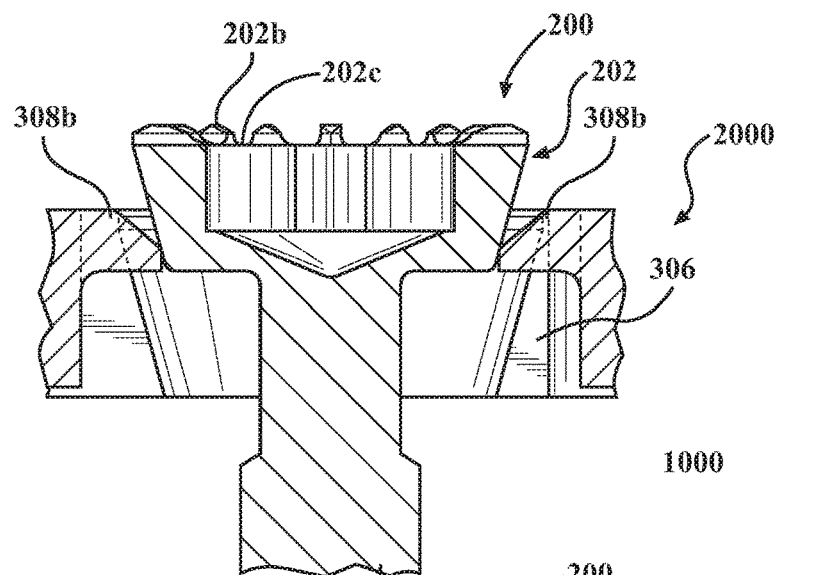
FIG. 13A is a cross-sectional view of FIG. 11 showing the head of the fastener pushing down on the retention member.
Figure 13B:
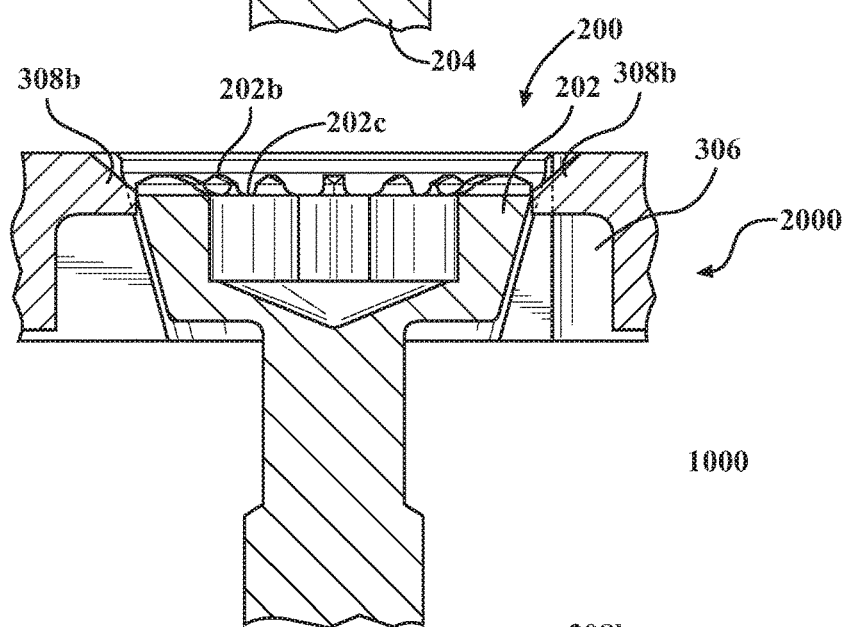
FIG. 13B is a view of FIG. 13A showing the fastener advancing.
Figure 13C:
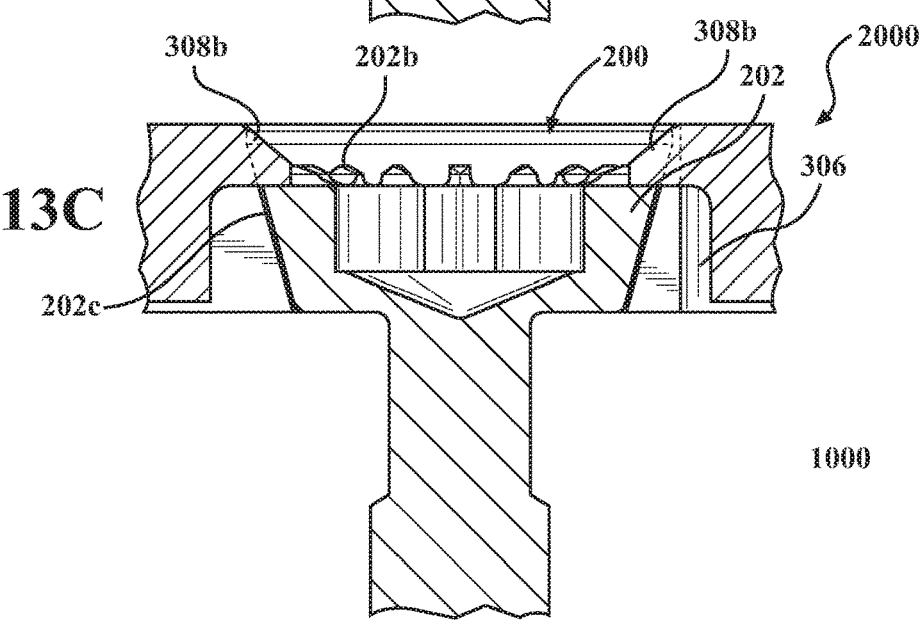
FIG. 13C is a view of FIG. 13B showing the retention member engaging the top surface of the fastener.

With reference now to FIGS. 13A-13C, an operation of the plate 300 is provided. Each end of the plate 300 may be mounted over adjacent vertebral bodies (not shown). As the operation of the retention members 308 is the same for the screws 200 in the vertebral openings 304 as the central opening 306 an illustration describing the central opening 306 is sufficient. FIG. 13A shows the head 202 of the screw 200 biasing the retention member 308 as the screw 200 advances into the central opening 306. As shown, both retention members 308 are biased away from the head 202. FIG. 13B shows the screw 200 advanced further. It should be appreciated that advancement of the screw 200 is done by turning the screw 200 so as to threadingly engage a reciprocating bore of an implant 1000. FIG. 13C shows the head 202 of the screw 200 seated against the implant 1000. As the head 202 is turned, the arms 308b of opposing retention members 308 are seated in a corresponding detent 202c so as to engage the head 202 of the screw 200 to prevent the screw 200 from rotating.

FIGS. 13A-13C also show how the depth of the openings 304, 306 are dimensioned so as to accommodate the head 202 of the screw 200. Thus, the head 202 of the screw 200 may be advanced past the arm 308b of the respective retention member 300. Though FIGS. 13A-13C show the central opening 306 registered to a threaded bore of an implant, the spatial dimensions illustrated may be applied to the vertebral openings 304 with respect to a vertebral body.

Figure 14:
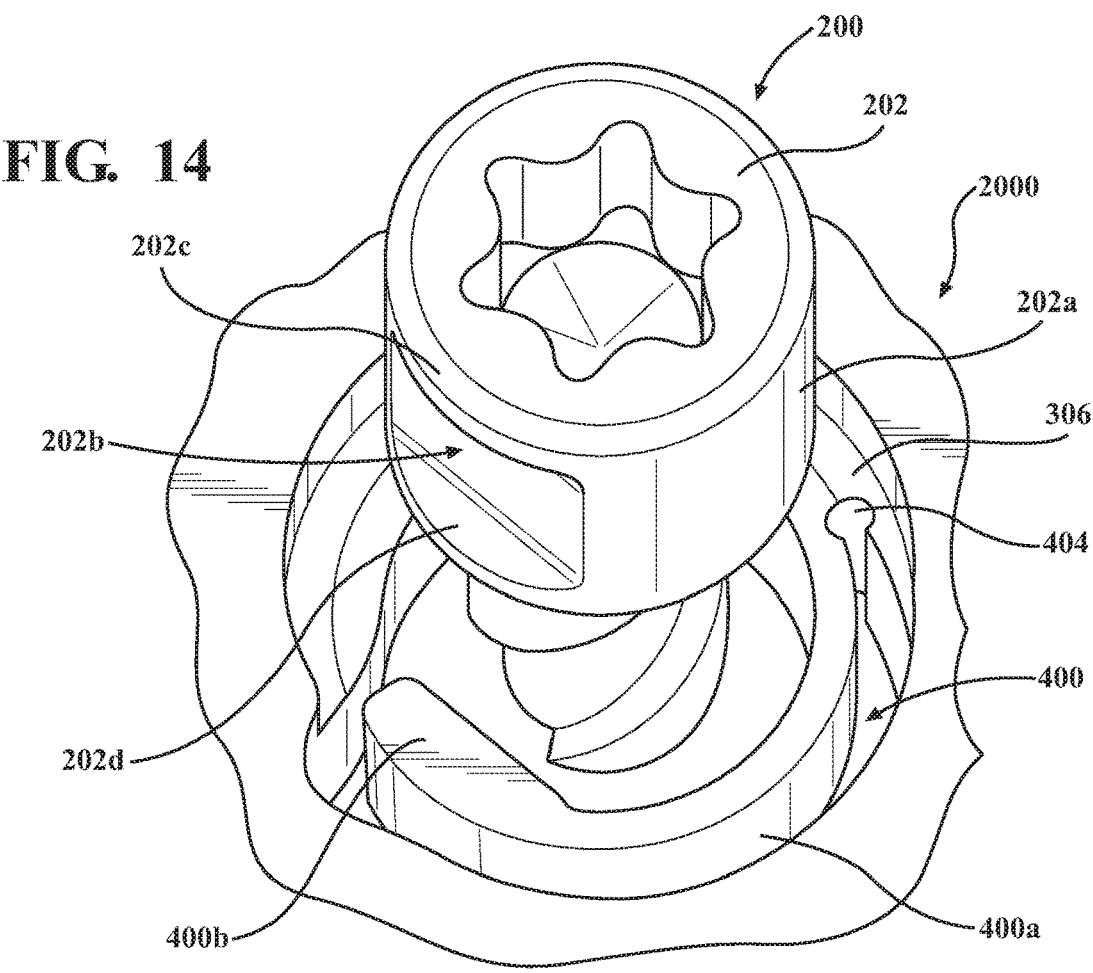
FIG. 14 is a perspective view of another embodiment of the fixation plate with a retention member configured to prevent the fastener from rotating.
Figure 15:
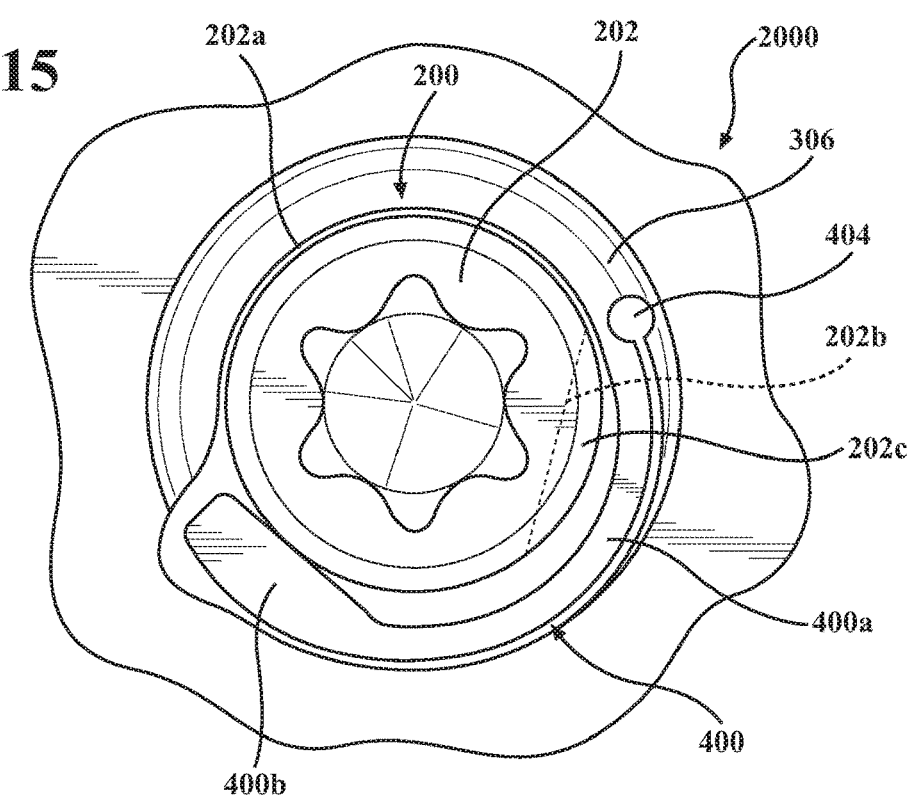
FIG. 15 is a top down view of FIG. 14 showing the retention member biased radially by the head of the fastener.
Figure 16:
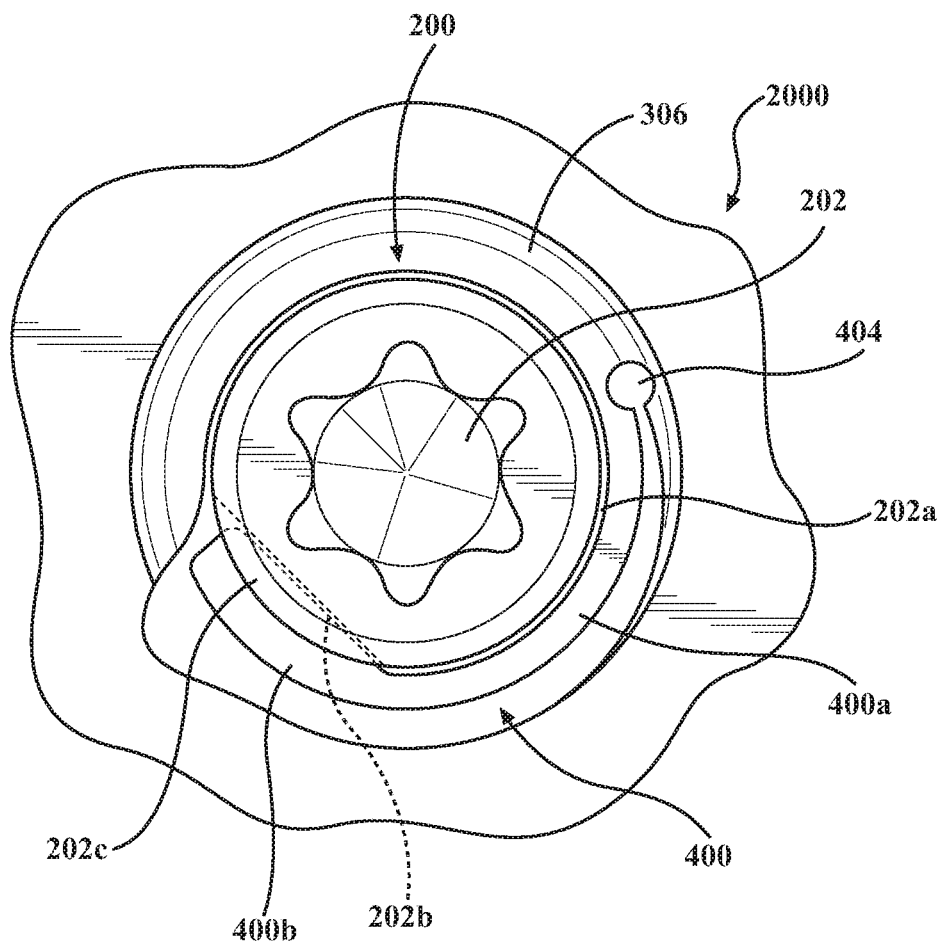
FIG. 16 is a top down view of FIG. 15 showing the retention member engaged with the fastener.

With reference now to FIGS. 14-16 another aspect of the fixation plate 300 and the retention member 408 as a resilient member disposed within an opening of the plate 300 is shown. It is understood that a cut-away view of the plate 300 is shown in FIGS. 14-16. FIGS. 14-16 provide isolated views of the opening 306 and the screw 200 to illustrate the operation of another aspect of the fixation plate 300 described above. As seen, a retention member 400 is illustratively shown as a curved arm having a flattened head. The proximal end of the curved arm is illustratively shown integrally formed to the body of the plate surrounding a respective opening. For illustrative purposes, the opening is shown as a central opening 406, however, the retention member 400 may also be used in a vertebral opening 406.

With reference first to FIG. 14, the retention member 400 includes an arm 400a which is curved so as to generally follow a portion of the central opening 406. A relief opening 404 is disposed adjacent the proximal end of the arm 400a so as to provide tolerance for biasing the arm 400a. In one embodiment, the relief opening 404 is a cylindrical bore extending between a top surface and bottom surface of the plate 300. The arm 400a includes an interior surface directly opposite the body of the plate 300 so as to be spaced apart from the body of the plate 300. The interior surface of the arm 400a is exposed to the central opening 406.

FIG. 15 also provides an illustrative embodiment of a screw 200 for engagement with the retention member 400. The screw 200 includes a head 202 having a side wall 202a. A portion of the side wall 202a includes a detent 202b. The detent 202b includes a flattened planar surface which is recessed with respect to the side wall 202a so as to define an upper lip 202c spaced apart from a lower lip 202d. The detent 202b is configured to engage a flattened head 400b of the arm 400a of the retention member 400.

FIG. 14 shows the retention member 400 in a natural state. FIG. 15 shows the retention member 400 biased against the inner wall of the plate 300 defining the central opening 306. In particular, as the screw 200 is advanced into the central opening 306 by rotation and engagement with a threaded bore of an implant (such as is generally shown in FIGS. 13A-13C), the head 202 of the screw 200 pushes the retention member 400 against the inner wall of the plate 300. FIG. 15 shows the detent 202*b* of the screw 200 offset from the flattened head 400*b* of the retention member 400. FIG. 16 shows the screw being advance further, wherein upon further rotation the flattened head 400*b* of the retention member 400 is engaged with the detent 202*b* of the screw 200. The plate 300 may have a central opening 306 with a depth similar to that shown in FIGS. 13A-13C so as to register the flattened head 400*b* of the retention member 400 with the detent 202*b* of the screw 200 when the screw 200 is seated against the implant.

With reference again to FIGS. 10-16 a system 2000 for use in a spinal procedure is provided. The system 2000 configured to prevent a fastener from backing out. The system 2000 includes a fixation plate having a retention member configured to engage the fastener, illustratively shown as a screw, so as to prevent the fastener from rotating and backing out.

FIGS. 10-13C illustrate one embodiment of the system 2000 wherein the fixation plate 300 is configured to be attached to a first vertebra (not shown) and a second vertebra (not shown) using a fastener, illustratively shown as bone screws 200. The fixation plate 300 may be substantially rectangular and include rounded sides and/or contoured surfaces to facilitate movement of tissue relative to the plate 300 after implantation in a patient.

The plate 300 is illustratively shown having a pair of vertebral openings 304 formed opposite ends of the plate 300. The vertebral openings 304 are configured to allow the screw 200 to find purchase in a vertebral body. A central opening 306 is disposed between the vertebral openings 304. The central opening 306 is configured to allow a screw 200 to find purchase in an implant 1000.

The plate 300 includes at least one retention member 308. For illustrative purposes, the plate 300 includes a pair of retention members 308. The retention members 308 are formed between the vertebral openings 304 and the central opening 306. The retention members 308 are configured to engage the screws 200 so as to prevent the screws 200 from rotating and backing out of the respective vertebral openings 304 and the central opening 306.

FIG. 10 shows a screw 200 being introduced into the central opening 306. It should be appreciated that the screw 200 shown in FIG. 10 may be modified for use to find purchase in vertebral bodies. In particular, the screws illustratively shown in FIG. 11 all have the same head 202 but the shafts 204 of the screws may differ to accommodate the intended use. For instance, the thread pitch and shape of the screw shown in FIG. 10 is intended to couple with an implant. However, the thread pitch and shape of screws intended to find purchase in a vertebral body may differ.

Referring again to FIG. 10 and also to FIG. 12, a perspective view and a top down view, respectively, of the plate 100 illustrates additional features of the retention member 300. The retention member 308 is a resilient material having a stem 308*a* and an arm 308*b*. The opposing sides of the stem 308*a* is spaced apart from the body of the plate 300 so as to form two slots 300*a* on each side of the stem 308*a*. The slots 308*a* allow the stem 308*a* to flex. The arm 308*b* extends into a respective opening. For illustrative purposes, the retention member 308 is shown as having two arms 308*b* extend into a respective vertebral opening 304 and central opening 306 so as to form the general shape of a "T".

The screw 200 includes a head 202 having a top surface 202*a* configured to engage an arm 308*b* of the retention member 308. In one embodiment top surface 202*a* includes a plurality of nubs 202*b* spaced apart from each other so as to form detents 202*c*. The arms 308*b* may include a taper 308*c*. The taper 308*c* may facilitate the introduction of the screw 200 into the vertebral body or the implant, as the case may be, by facilitating the biasing of the retention member 308 about the stem 308*a*. The screws include a shaft 304 with a thread 304*a*. As described above, the thread 304*a* is shown configured to couple with an implant, but may be modified to find purchase with a vertebral body.

The retention members 308 are configured to engage the top surface 202*a* of the screw 200 so as to prevent the screw 200 from rotating. In one embodiment, the arm 308*b* of the retention member 308 is configured to be seated in a detent 202*c* so as to be nestled between adjacent nubs 202*b* wherein the rotation of the screw 200 is prevented by the nubs 202*b* restricting the movement of the arm 308*b*.

Another embodiment of the system 2000 is illustratively shown in FIGS. 14-16, wherein the retention member 400 is illustratively shown as a curved arm having a flattened head. The proximal end of the curved arm is illustratively shown integrally formed to the body of the plate surrounding a respective opening. For illustrative purposes, the opening is shown as a central opening 406, however, the retention member 400 may also be used in a vertebral opening 406.

With reference first to FIG. 14, the retention member 400 includes an arm 400*a* which is curved so as to generally follow a portion of the central opening 406. A relief opening 404 is disposed adjacent the proximal end of the arm 400*a* so as to provide tolerance for biasing the arm 400*a*. In one embodiment, the relief opening 404 is a cylindrical bore extending between a top surface and bottom surface of the plate 300. The arm 400*a* includes an interior surface directly opposite the body of the plate 300 so as to be spaced apart from the body of the plate 300. The interior surface of the arm 400*a* is exposed to the central opening 406.

FIG. 15 also provides an illustrative embodiment of a screw 200 for engagement with the retention member 400. The screw 200 includes a head 202 having a side wall 202*a*. A portion of the side wall 202*a* includes a detent 202*b*. The detent 202*b* includes a flattened planar surface which is recessed with respect to the side wall 202*a* so as to define an upper lip 202*c* and lower lip 202*d*. The detent 202*b* is configured to engage a flattened head 400*b* of the arm 400*a* of the retention member 400.

FIG. 14 shows the retention member 400 in a natural state. FIG. 15 shows the retention member 400 biased against the inner wall of the plate 300 defining the central opening 306. In particular, as the screw 200 is advanced into the central opening 306 by rotation and engagement with a threaded bore of an implant (such as is generally shown in FIGS. 13A-13C), the head 202 of the screw 200 pushes the retention member 400 against the inner wall of the plate 300. FIG. 15 shows the detent 202*b* of the screw 200 offset from the flattened head 400*b* of the retention member 400. FIG. 16 shows the screw being advance further, wherein upon further rotation the flattened head 400*b* of the retention member 400 is engaged with the detent 202*b* of the screw 200. The plate 300 may have a central opening 306 with a depth similar to that shown in FIGS. 13A-13C so as to register the flattened head 400b of the retention member 400 with the detent 202b of the screw 200 when the screw 200 is seated against the implant.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A bone fixation system comprising a plate and a fastener,
   wherein the fastener has a head at a proximal end, the head having a top surface including a plurality of proximally extending nubs spaced apart from each other so as to form corresponding detents between each of the nubs on the top surface of the head;
   wherein the plate is configured to receive the fastener and has an opening configured to receive the head of the fastener; and
   wherein the plate comprises a retention member having a stem and a first arm and a second arm each roughly orthogonal to the stem, the stem mounted to an inner surface of a body of the plate adjacent the opening and being formed of a resilient material so as to allow the fastener to pass, wherein the first arm extends over at least a portion of the top surface of the head and a distal end of the first arm engages one of the corresponding detents of the top surface of the head so as to resist rotation of the fastener and wherein the first arm is configured to execute a top down engagement of the top surface of the head of the fastener so as to prevent the fastener from backing out; and
   wherein the stem and first and second arms form the general shape of a "T" each end of the "T" configured to extend into a separate opening of the plate so as to simultaneously secure two or more fasteners.

2. The system as set forth in claim 1, wherein the first arm extends into the opening.

3. The system as set forth in claim 1, wherein the opening includes a pair of vertebral openings and a central opening, the vertebral openings formed on opposite ends of the plate and the central opening disposed between the vertebral openings.

4. The system as set forth in claim 3, including a pair of retention members, each of the pair of retention members having a stem and a pair of arms, each of the stems disposed between the central opening and a respective vertebral opening, wherein one of the pair of arms extends into a respective vertebral opening and each of the other of the pair of arms extends into the central opening.

5. The system as set forth in claim 1, wherein the retention member and the plate body comprise the same material.

6. The system as set forth in claim 1, wherein the retention member is integrally formed with the body of the plate.

7. The system as set forth in claim 1, wherein the arm engages one of the corresponding detents of the top surface of the head so as to stop rotation of the fastener.

8. The system as set forth in claim 1, further comprising a second fastener and the plate further comprising a second opening configured to receive the second fastener,
   wherein the second fastener has a head at a proximal end, the head having a top surface including a plurality of proximally extending nubs spaced apart from each other so as to form corresponding detents between each of the nubs; and
   wherein the retention member further comprises a second arm extending from the stem, the second arm configured to extend over at least a portion of the top surface of the head of the second fastener and engage one of the corresponding detents of the top surface of the head so as to resist rotation of the second fastener.

9. A system for preventing a fastener from backing out, the system comprising:
   a fastener having a head and a shaft, wherein the head has a top surface and a smooth peripheral sidewall, the top surface including a plurality of upward-facing nubs spaced apart from each other so as to form corresponding detents between each of the plurality of nubs;
   a plate having an opening configured to receive the fastener, the plate having a retention member having a stem and at least two arms one of which is generally orthogonal to the stem, the stem mounted to an inner surface of a body of the plate adjacent the opening and being formed of a resilient material so as to be deformable to allow the fastener to pass into the opening and returning to a non-deformed position in which one arm prevents unintended backing out of the fastener, wherein one arm engages one of the corresponding detents of the top surface of the head so as to resist rotation of the fasteners;
   wherein each arm extends into a separate opening of the plate so as to simultaneously secure two or more fasteners.

10. The system as set forth in claim 9, wherein the at least one arm extends into the opening.

11. The system as set forth in claim 9, wherein the opening includes a pair of vertebral openings and a central opening, the vertebral openings formed on opposite ends of the plate and the central opening disposed between the vertebral openings.

12. The system as set forth in claim 11, including a pair of retention members, each of the pair of retention members having a stem and a pair of arms, each of the stems disposed between the central opening and a respective vertebral opening, wherein one of the pair of arms extends into a respective vertebral opening and each of the other of the pair of arms extends into the central opening.

13. The system as set forth in claim 9, wherein the retention member and the plate body comprise the same material.

14. The system as set forth in claim 9, wherein the retention member is integrally formed with the body of the plate.

15. The system as set forth in claim 9, wherein the arm engages one of the corresponding detents of the top surface of the head so as to stop rotation of the fastener.

16. The system as set forth in claim 9, further comprising a second fastener and the plate further comprising a second opening configured to receive the second fastener,
   wherein the second fastener has a head at a proximal end, the head having a top surface including a plurality of proximally extending nubs spaced apart from each other so as to form corresponding detents between each of the nubs; and
   wherein the retention member further comprises a second arm extending from the stem, the second arm configured to extend over at least a portion of the top surface of the head of the second fastener and engage one of the corresponding detents of the top surface of the head so as to resist rotation of the second fastener.

\* \* \* \* \*